United States Patent
Verdegan et al.

[19]

[11] Patent Number: 5,968,371
[45] Date of Patent: Oct. 19, 1999

[54] LUBRICANT CIRCULATION DIAGNOSTIC AND MODELING SYSTEM

[75] Inventors: Barry M. Verdegan, Stoughtin; Larry J. Eriksson, Madison, both of Wis.

[73] Assignee: Nelson Industries, Inc., Stoughton, Wis.

[21] Appl. No.: 09/013,531

[22] Filed: Jan. 26, 1998

[51] Int. Cl.[6] .................... B01D 17/12; G01N 33/26
[52] U.S. Cl. ............ 210/739; 73/53.05; 73/53.07; 184/6.24; 184/108; 210/85; 210/90; 210/93; 210/94; 210/96.1; 210/168; 210/741; 210/805; 210/791; 340/603
[58] Field of Search ................. 210/85, 90, 93, 210/94, 96.1, 103, 143, 168, 171, 739, 741, 745, 746, 805, 97, 100, 149, 742, 791; 123/196 A; 184/6.24, 108; 73/53.05, 53.07; 340/603, 606, 611

[56] References Cited

U.S. PATENT DOCUMENTS

| | | | |
|---|---|---|---|
| 4,677,676 | 6/1987 | Eriksson | 381/71 |
| 4,685,066 | 8/1987 | Hafele et al. | 210/90 |
| 4,852,693 | 8/1989 | Nakajima et al. | 184/108 |
| 4,987,598 | 1/1991 | Eriksson | 381/71 |
| 5,095,740 | 3/1992 | Hodgson et al. | 210/340 |
| 5,172,416 | 12/1992 | Allie et al. | 381/71 |
| 5,386,477 | 1/1995 | Popovich et al. | 381/71 |
| 5,396,561 | 3/1995 | Popovich | 381/71 |
| 5,462,679 | 10/1995 | Verdegan et al. | 210/798 |
| 5,557,682 | 9/1996 | Warner et al. | 381/71 |
| 5,561,598 | 10/1996 | Nowak et al. | 381/71 |
| 5,586,189 | 12/1996 | Allie et al. | 381/71 |
| 5,586,190 | 12/1996 | Trantow et al. | 381/71 |
| 5,604,441 | 2/1997 | Freese et al. | 73/53.05 |
| 5,702,592 | 12/1997 | Suri et al. | 210/90 |

OTHER PUBLICATIONS

"Resistance to Flow of Liquids in Fibrous Beds Applied To Cartridge Filtration", Jaisinghani and Sprenger, *Filtration and Separation*, Mar./Apr. 1981, Uplands Press Limited, 2 Woodstock Road, Croydon CR9 1LB England.

"Least–Squares Fit To An Arbitrary Function", Bevington, *Data Reduction And Error Analysis For The Physical Sciences*, pp. 204–213, McGraw–Hill Book Company, New York, 1969.

*Primary Examiner*—Joseph W. Drodge
*Attorney, Agent, or Firm*—Andrus, Sceales, Starke & Sawall

[57] ABSTRACT

A lubricant filtering and monitoring system and method is provided for a lubricant circulation system circulating lubricant through a filter to a lubricated component. A combination of sensors senses a condition of the lubricant before and after passage through the filter and before and after passage through the component and provides an output indicative of a condition in the circulation system. A sensor senses a condition of lubricant flowing through the filter, and another sensor senses a condition of lubricant flowing through a reference section for comparison against and normalizing of the output of the first sensor. A method of actively monitoring the component is provided by comparing influent to the component with effluent from the component to ascertain how lubricant is being modified by the component, by sensing a condition of lubricant passing through the filter. An effective method is provided for determining when to change or clean the filter. A diagnostic method is provided for assisting in such determination and diagnosing lubricant condition, filter condition and component condition.

29 Claims, 3 Drawing Sheets

LUBRICANT CIRCULATION DIAGNOSTIC AND MODELING SYSTEM

BACKGROUND AND SUMMARY

The invention relates to lubricant circulation systems circulating lubricant through a filter to a lubricated component, such as an internal combustion engine, and more particularly to diagnostic systems and methods, including using the filter as a sensor, combinations of sensors for condition indication, and active monitoring of the lubricated component by sensing a condition of lubricant flow through the filter.

Lubrication systems, including hydraulic and lube oil systems, typically include a circulation system circulating lubricant through a filter to a lubricated component such as an engine. Contamination is controlled by the filter. Regular cleaning or changing of the filter ensures that the filter continues to perform its function. This type of contamination control system assumes that the filter has appropriate removal, restriction and capacity characteristics. This may be verified by spot checking, e.g. lubricant analysis.

Servicing of the filter is the responsibility of the operator. This approach has shortcomings. Firstly, the life of the filter may be longer or shorter than the scheduled interval. In either case, there is an economic penalty, namely excessive wear or premature disposal of filters, when the scheduled interval differs from the actual life of the filter. Secondly, operators do not always service the filters when required. Thirdly, spot checking the contamination levels may not identify problems soon enough, especially if confirmation of a problem is sought before corrective action is taken. In one aspect, the present invention addresses and solves these limitations by integrating the filter with contamination monitoring devices in a control system that continuously evaluates contamination levels.

A wide variety of lubricated components, including various types of machinery and engines benefit from preventative maintenance procedures in order to avoid unexpected downtime and major repairs. In one aspect, the present invention uses the filter as part of an active monitoring system. The filter is not merely a device for removal of undesired contaminants, but is also a sensor used in determining engine or other lubricated component condition. Filters/separators in engine flow streams such as lubricating oil lines, remove particles and adsorb/absorb chemical compounds that are analyzed to determine engine condition on an off-line or on-line basis. The filter system is controlled on a time-varying basis to preferentially remove specific contaminants to optimize the amount of information that may be obtained about the engine. The oil flow is used as a means to actively probe the engine, with the filter collecting the results of the probing. In addition to comparing the influent into the filter with the effluent from the filter, the focus is on how the influent into the engine is modified by the engine and compares to the effluent from the engine. This is accomplished by sensing a condition of lubricant flow through the filter. The filter may have various sensors installed to measure and analyze the effluent from the engine for wear products such as various metals as well as for change in chemical composition due to wear and aging. Such sensors include contamination monitors, turbidimeters, capacitance sensors, dielectric constant sensors, optical monitors including particle counters, spectrometers. Some of the sensors may be constructed from the filter media itself such as a conductivity measurement through metallic fibers.

In another aspect of the invention, an effective system and method are provided for determining when to change or clean the filter. The invention is particularly useful in combination with cleanable and/or easy change filters such as shown in commonly owned U.S. Pat. No. 5,462,679 and commonly owned co-pending U.S. applications Ser. No. 08/755,479, filed Nov. 22, 1996, Ser. No. 08/755,497, filed Nov. 22, 1996, now U.S. Pat. No. 5,779,900, and Ser. No. 08/819,296, filed Mar. 18, 1997, now U.S. Pat. No. 5,858,224. There are numerous devices known in the prior art to indicate when to change a filter. Most indicate the pressure drop across the filter, e.g. by a pressure gauge, and signal that it is time to change the filter. This approach is inadequate in numerous applications, particularly where it is desirable to schedule filter service at a convenient time. The noted prior art devices indicate that it is time to change the filter, not how long it is until a change need be made. The present invention provides a smart system telling the user how long it is until a change is needed. This enables the operator to schedule filter servicing well in advance and at convenient times. This also enables the operator to keep track of filter life, and to have a method of early detection of filter failures, and have an idea of the severity of the operating environment and its impact on the filters and the lubricated equipment, and to optimize filter service intervals, thus saving time and money.

The present invention integrates a cleanable and/or changeable lubricant filter with component condition monitoring, lubricant condition monitoring, and filter condition monitoring. Cleaning accomplishes little if it is done too late and the pressure drop across the filter is too high. On the other hand, if done too early, it wastes lubricant. Cleaning could be done on a regular time or mileage or other usage factor basis, but unusual conditions could produce excessive pressure drop and result in ineffective cleaning. Component or engine operators are striving for increasing long lubricant change intervals, and this places greater demand on the lubricant which in turn can produce sludge that irreversibly plugs the filter. Hence, it is also desirable to monitor lubricant quality. This not only ensures cleaning effectiveness, but also signals the operator when to change lubricant, thus reducing engine wear and maintenance problems. In one aspect, the present invention addresses and solves this need by providing at least three types of information, namely filter time or miles, filter pressure drop, and an independent measure of lubricant quality.

It is easy to initiate filter cleaning or alert the operator of this need based on time or miles of usage and/or differential pressure across the filter. Differential pressure is a function of lubricant condition, filter usage, duty cycle, and temperature. The latter two are transient conditions, but the former two could provide useful information about the condition of the filter and lubricant. As such, differential pressure has the potential to provide diagnostic information about the component or equipment to the operator. Lubricant condition typically changes relatively slowly. The change in differential pressure, or other monitored parameter, is often more diagnostic than the actual values of the parameter itself. Deviations from the expected behavior and predictions made on the basis of differential pressure behavior are valuable diagnostic tools. The problem with using differential pressure data to evaluate lubricant quality is that for most of the filter's life, differential pressure is so low, FIG. 2, that useful interpretation of the results cannot be made. Also, this only provides an indication of the solid contaminants in the lubricant. Therefore, it is advantageous to monitor additional parameters to more accurately assess lubricant condition.

In one aspect of the present invention, lubricant condition is monitored in various ways. Sensors measuring light absorbance at a particular wavelength, capacitance, temperature, and viscosity are among these. It is known in the prior art to calculate lubricant condition based on engine operating time and oil temperature. Instantaneous measurements of a single lubricant parameter are susceptible to transients, do not consider how the lubricant has changed over time, and ignore other measures of lubricant quality. On the other hand, the calculated condition makes assumptions about engine conditions that may not reflect reality. In one embodiment, the present invention uses the filter, two differential pressure sensors, a temperature sensor, and an additional sensor provided by either a flow rate or viscosity sensor, to monitor lubricant, filter and component status. The filter is preferably a cleanable filter, but could be a disposable filter. The temperature sensor monitors the lubricant temperature at a point near the differential pressure sensors. One of the differential pressure sensors monitors differential pressure across the filter, and the other differential pressure sensor monitors differential pressure across a reference section. The second differential pressure sensor normalizes the output of the first differential pressure sensor for flow and viscosity changes. The remaining sensor, if a viscosity sensor, measures viscosity, an indicator of lubricant condition, and enables the flow rate to be calculated from the second differential pressure sensor's output. If the remaining sensor is a flow rate sensor, it enables viscosity to be calculated from the second differential pressure sensor's output. The combination of sensors yields filter differential pressure, flow rate, temperature, and viscosity data. The data is collected and evaluated at engine start-up and used to calculate the viscosity index, VI, of the lubricant, another useful measure of lubricant condition.

In further aspects, the filter differential pressure results are used to estimate contaminant concentration, once the differential pressure is high enough. The filter usage, e.g. time or mileage, and the differential pressure results indicate when the filter needs to be cleaned or replaced, and can be used to notify the operator or trigger a cleaning cycle. Lubricant viscosity, whether calculated or measured, is a direct measure of lubricant quality. Viscosity changes are linked to lubricant breakdown. Viscosity index provides a more detailed measure of lubricant quality and is useful in identifying problems, including sludge formation and breakdown of viscosity index improvers, that directly impact filter performance and cleanability. A particularly advantageous feature is the use of changing oil viscosity and temperature as the equipment or engine warms up to calculate the viscosity index. In a number of engine applications, particularly off-road dump trucks, garbage trucks, etc., sludge formation has been linked to the viscosity index improvers in the oil and extended oil drain intervals. Flow rate data can reveal when and how long the filter is in a bypass mode. This is useful in anticipating wear related problems. Time and temperature data are used to estimate lubricant condition. Temperature alone can be used to identify overheating and potential cooling problems. By monitoring changes in viscosity and viscosity index over time, lubricant service intervals can be optimized. The noted data, including viscosity, viscosity index, temperature, time, flow rate, estimated contaminant concentration, provide a much more accurate assessment of the condition of the filter and lubricant, and their service requirements, which in turn optimizes maintenance requirements.

In further embodiments, various combinations of sensors are used, including optical contamination monitors. In addition, pressure differential sensors may optionally be incorporated. The filter may be any type suitable for the application, for example pleated cellulose or synthetic cartridge filters. The contamination monitor may be a simple nephelometer or turbidimeter. As known, the device shines light through the flowing lubricant while a detector oriented at an angle, typically 30–150°, from the angle of incidence measures the amount of light scattered from the lubricant. In one aspect, a monitor or sensor display can simply indicate the need for a filter change or cleaning when a predetermined differential pressure is reached. Depending on how fast the differential pressure rose, the monitor or sensor display can also recommend that a different type of filter be used. The contamination monitor, such as the turbidimeter, provides additional diagnostic analysis. Turbidity correlates directly to contamination levels. Over time, the amount of scattered light may remain constant or gradually climb under normal conditions. However, additional information can be obtained by tracking the amount of light scattered over short time intervals, e.g. milliseconds. Under normal conditions, the signal would oscillate noisily about a mean. Turbidimeters typically use relatively long integration times to eliminate the effects of noise. However, in one aspect of the present invention, short integration times are used to detect short-lived excursions outside the normal noise range. These excursions indicate the presence of large or highly reflective particles, which increase the amount of light scattered or reflected to the detector, in the sensing zone. Such particles are normally present at very low concentrations and such excursions would be uncommon. However, increased frequency of the excursions or increases in their magnitude would indicate an abnormal, undesirable situation, such as imminent catastrophic failure, leakage or unloading of the filter, gross external contamination.

In one aspect, the output of the noted optical monitors contain three types of information. Firstly, the baseline is an indication of the gross contamination level of the system, i.e. solids concentrations. Secondly, the amplitude and frequency of excursions indicates the presence of large and shiny particles. These excursions are of short duration. Their frequency is a function of the sensing volume, flow rate, and concentration of such particles. Thirdly, there is noise due to engine or component vibration and environmental factors. This contribution has frequency and rise time characteristics different from the excursions and baseline information. A controller makes its evaluations based on the first two types of information while minimizing the effects of the third type on the results. The resultant controller output is used to indicate problems and possible corrective action for disposable filter systems. In the case of a cleanable filter, there is additionally initiated a cleaning cycle. Depending on the number and locations of the sensors, problems can be isolated and corrective action taken before larger problems develop. For example, increased excursions by a sensor downstream of the filter suggests problems associated with the filter. Such an occurrence from a sensor upstream of the filter indicates gross external contamination. For a sensor located in a return line from the component or engine, excessive wear is indicated.

In further aspects of the invention, the noted active monitoring is extended to active probing of the lubricated component or engine by the addition of specific particulates, chemicals, radioactive materials, or similar materials in order to determine the effect of the engine or component on their passage. The use of such probe substances, typically only in trace quantities, or at least in quantities not harmful to the component or engine, along with the filtration and analysis above noted, provides diagnosis and evaluation of the condition of flow passages through an engine as well as detection of the presence of other materials in the engine through their interaction with the probe material and subsequent removal and analysis by the filter system. The quantity and quality of probe material may be varied over time to provide additional information about the engine or component.

In another aspect, in addition to actively using the filter for sensing and/or probing an engine or component, the filter system is used to actively control lubricant flow through the engine or component to provide yet more information on the need for preventative maintenance. In one embodiment, the lubricant stream flow is modulated to enhance the ability of the monitoring system to learn more about the behavior and condition of the engine. Other physical parameters, including temperature, acidity, etc., are similarly modified on a controlled basis to allow small fluctuations from the base level. Modulation of the flow stream or one of its physical parameters allows measurement of the response characteristics of the lubricated component or engine as well as the filter system on a dynamic basis. These response characteristics can be related to lubricant condition, filter condition, and component condition. The dynamic signals can be measured using the appropriate sensor such as a pressure sensor and processed using digital signal processing and adaptive control technology to perform a time domain system identification procedure. The least means squares (LMS) algorithm may be used in the modeling algorithm. The system identification procedure results in a set of digital coefficients that model the combined system response. Alternatively the system response characteristics can be determined through frequency domain techniques using various forms of the Fast Fourier Transform (FFT).

In a further embodiment, the filtration system is equipped with two differential pressure sensors and a timer. One of the differential pressure sensors measures the restriction across the filter. This sensor provides a direct indication of the amount of the filter's total capacity which has been used. The second differential pressure sensor measures differential pressure across a reference section such as a flow section, orifice, length of tubing or fixed restriction. The second sensor's output is used to normalize the differential pressure data from the first sensor to a constant flow rate and viscosity. Ideally, separate flow rate and viscosity sensors are used, but this adds cost and complexity to the system. For liquid filters, differential pressure is proportional to the product of flow rate and viscosity to a good first approximation, Jaisinghani and Sprenger, "Resistance To Flow Of Liquids In Fibrous Beds Applied To Cartridge Filtration", *Filtration and Separation*, March/April, 1981, Uplands Press Limited, 2 Woodstock Road, Croydon CR9 1LB, England. This is also true in laminar capillary flow. Hence, a single sensor may be used, for cost effectiveness, to provide the data to correct for varying flow rate and viscosity, as above noted.

The estimated remaining useful life, RUL, and the estimated total useful life, TUL, of the filter can be calculated based on a curve fitting algorithm, Bevington, "Least-Squares Fit To An Arbitrary Function", *Data Reduction And Error Analysis For The Physical Sciences*, pp. 204–213, McGraw-Hill Book Company, New York, 1969, and input from the sensors and timer. Multipass tests for a variety of filter media and filters show that differential pressure data all follow a similar function, provided that the influent concentration and contaminant are constant. The form of the function and the regression equation to solve for the constants are programmed into a controller. The controller accepts data from both differential pressure sensors and uses the data from the second sensor to normalize the differential pressure data from the first sensor. The normalized differential pressure data and the time data are stored for a particular filter change, and the results are used to calculate RUL and TUL on a near continuous basis. The accuracy of RUL and TUL are relatively poor early in filter life, but become increasingly accurate as the filter starts plugging. An output signal from the controller is used to provide a display for the operator and/or initiate filter cleaning and/or some other function. RUL enables the operator to plan when to service the filter. TUL provides the operator with an idea of how long the filter is lasting and how it compares with similar data for other filter changes. If the filter is a cleanable filter, the RUL and TUL data are used to automatically initiate the cleaning mode. Cleaning occurs when RUL is a given percentage of TUL, preferably 10 to 20%.

The algorithm and use of the sensors and timer to calculate RUL and TUL are based on a number of assumptions. These include: firstly, that differential pressure is proportional to the product of flow rate and viscosity; secondly, constant contaminants; thirdly, constant influent concentration; fourthly, the filter behaves normally. Based on Jaisinghani and Sprenger's work, above noted, the error associated with the first assumption is expected to be less than 15% for lube and hydraulic oil filters. The second assumption may be violated if a coolant leak occurs in an engine, sudden catastrophic failure of a component occurs, the equipment is used in drastically different environments, or during other abnormal transient conditions, otherwise the second assumption should be valid. The third assumption is probably the weakest. For over-the-road trucks and stationary engines, it is likely valid. For construction and agricultural equipment, environmental conditions can change rapidly. The air and oil filters can dampen the effects of these changes, but variations will occur. If the controller calculates the correlation coefficient r for the differential pressure versus time function, in addition to RUL and TUL, the validity of this assumption can be tested and it is possible to modify the algorithm to account for the changes in contaminant loading. The noted regression equation is programmed into the controller, and the controller solves for the regression constants. At any given point in time, the regression constants provide a measure of the time-weighted influent concentration. The correlation coefficient r provides one test of the validity of the assumption of constant concentration. A poor r is indicative of variable concentration. A comparison of the observed normalized pressure drop and the normalized pressure drop calculated from the regression constants can be used to identify transient conditions and changes in the operating environment or equipment. A significant variance between observed and calculated normalized pressure drops is indicative that the concentration has changed appreciably, which could mean operation in a dirtier environment, failure of the air cleaner, a change in engine condition, a failure of the oil filter, etc. Changes in contaminant loading are indicated by the magnitude of the difference between the calculated and observed normalized pressure drops or contaminant concentrations. The fourth assumption is valid except when filter integrity is violated, e.g. when leaks or filter bypassing occurs. Evaluation of the historical data for the filter, looking for evidence of discontinuities or failure of differential pressure to increase, provides the operator with useful diagnostics not readily available by other means.

The present invention uses differential pressure as a gauge in assessing filter life in one embodiment. In other embodiments, other aspects are used instead of or in combination with differential pressure, such as turbidity, particle count, conductivity, etc., as above noted. This involves a trade-off of increased diagnostic analysis capability versus cost. In other embodiments, a system identification technique can be used with either the differential pressure approach or with the measurement of other physical or chemical parameters.

DETAILED DESCRIPTION

Figure 1:
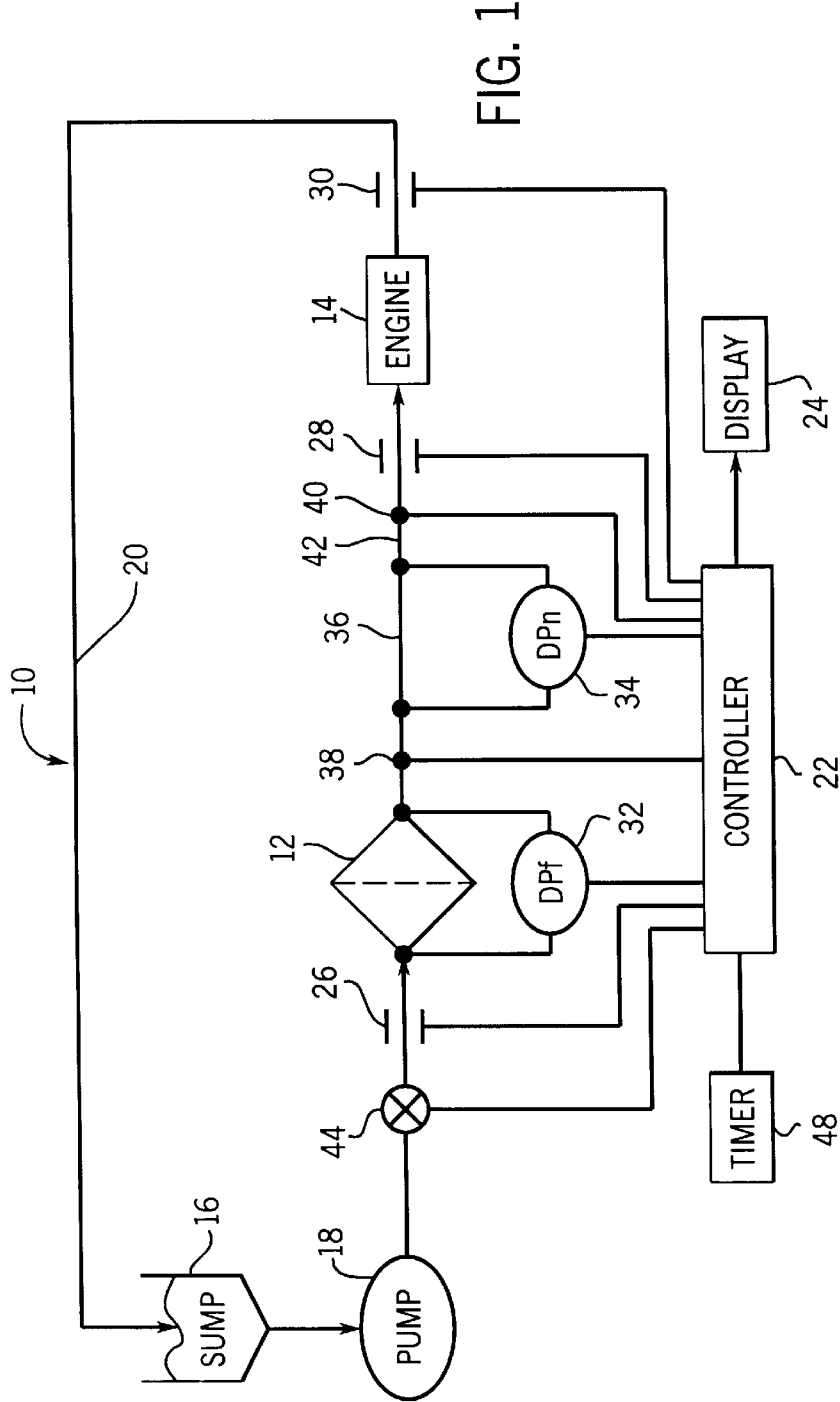
FIG. 1 is a schematic illustration of a lubrication system in accordance with the invention.

FIG. 1 shows a lubrication system including a circulation system 10 circulating lubricant through a filter 12 to a lubricated component 14 such as an internal combustion engine. The system includes a sump 16 providing a collection reservoir for lubricant, a pump 18 pumping lubricant from sump 16 through filter 12 to component or engine 14, and a return line 20 returning lubricant from engine 14 to sump 16. A combination of sensors, to be described, senses one or more conditions of the lubricant before and after passage through filter 12 and before and after passage through engine 14 and provides an output to programmable controller 22 and display 24 indicative of a condition in the circulation system. Controller 22 may be digital or analog, and display 24 may include light emitting diodes, LEDs, a liquid crystal display, LCD, or the like.

A first sensor 26 is provided between pump 18 and filter 12. A second sensor 28 is provided between filter 12 and engine 14. A third sensor 30 is provided between engine 14 and sump 16. In one embodiment, each of sensors 26, 28, 30, is a contamination monitor, preferably an optical monitor provided by a turbidimeter. A fourth sensor is provided by a pressure differential sensor 32 sensing differential pressure across the filter, DPf. A fifth sensor is provided by a pressure differential sensor 34 sensing differential pressure DPr across a reference section 36, provided by a designated flow section, orifice, length of tubing or fixed restriction, for normalizing DPf, to be described. Reference section 36 in circulation system 10 passes lubricant therethrough during circulation thereof. Sensor 32 senses a condition of lubricant flow through filter 12, namely differential pressure thereacross, i.e. pressure drop $\Delta P$ there across. Reference section 36 is of given restriction and receives lubricant from filter 12. Sensor 34 senses differential pressure across reference section 36. A further sensor is provided by temperature sensor 38 sensing lubricant temperature at sensors 32 and 34. A yet further sensor 40 is provided by a viscosity sensor sensing lubricant viscosity. In an alternate embodiment, sensor 40 is provided by a lubricant flow rate sensor.

Lubricated component 14 in circulation system 10 is actively monitored by circulating lubricant through filter 12 to component 14, by comparing influent to component 14 with effluent from component 14 to ascertain how lubricant is modified by component 14, by sensing a condition of lubricant passing through filter 12. This is accomplished by a plurality of sensors sensing a condition of the lubricant before and after passage through component 14 and before and after passage through filter 12. Path 42 passes lubricant from filter 12 to component 14.

Path 20 passes lubricant from component 14 to sump 16 and pump 18 back to filter 12. A first set of one or more sensors in path 42 senses a condition of the lubricant after passage through filter 12 and before passage through component 14. A second set of one or more sensors in path 20 senses a condition of the lubricant after passage through component 14 and before passage through filter 12. In one embodiment, the flow of lubricant to component 14 is modulated, by valve 44 in or in series with filter 12, to facilitate sensing and test the active monitoring.

Figure 2:
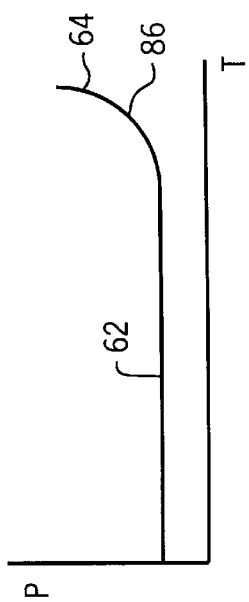
FIG. 2 is a graph illustrating changes in a known filter characteristic over time.
Figure 3:
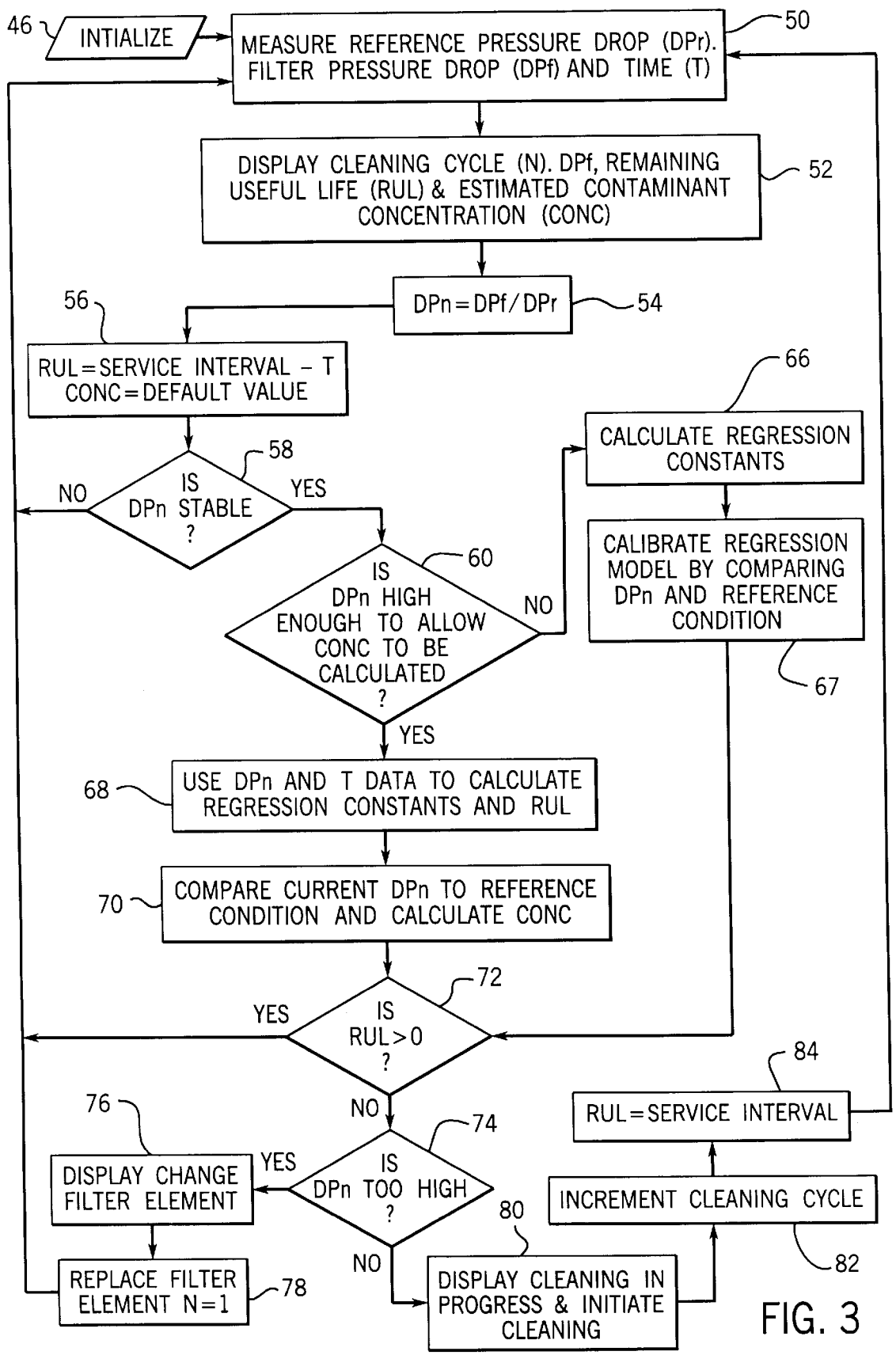
FIG. 3 is a flow chart illustrating steps for determining whether to replace or clean the filter.

The filter is used as a sensor to sense a given condition of lubricated component 14 by sensing a condition of lubricant passing through the filter as an indication of the given condition of lubricated component 14. Referring to the flow chart in FIG. 3, there is illustrated the method for sensing a condition of lubricant flowing through filter 12 with sensor 32, providing a reference section 36 and sensing a condition of lubricant flowing through the reference section with sensor 34, and comparing the outputs of sensors 32 and 34 and determining a given condition in circulation system 10. The output of sensor 34 is used to normalize the output of sensor 32. The system is initialized at 46, as shown in FIG. 3, in controller 22, followed by measurement of the reference pressure drop DPr by sensor 34, filter pressure drop DPf by sensor 32, and elapsed time as timed by timer 48, as shown at block 50. The cleaning cycle number is displayed in display 24, together with DPf, remaining useful life RUL, and estimated contaminant concentration CONC, to be described, block 52. Normalized differential pressure DPn is then determined according to the ratio of DPf to DPr, block 54. Remaining useful life, RUL, is determined according to service interval minus elapsed time, block 56, and CONC is determined according to a default value, to be described. A determination is then made as to whether DPn is stable, step 58. If not, the above steps are repeated. If so, then a determination is made whether DPn is above a given value high enough to allow contaminant concentration CONC to be calculated, step 60. As illustrated in FIG. 2 showing pressure drop versus time for typical filters 12, the differential pressure across the filter during most of its life is too low as shown at 62 to enable meaningful concentration calculation, i.e. the pressure drop does not start to build up until later in filter life as shown at 64. If DPn is not high enough to allow CONC to be calculated, then the regression constants are calculated, block 66, for the noted algorithm to fit the function for the filter such as shown in FIG. 2, and the next step is to compare DPn and the reference condition, block 67, to calibrate the regression model to adjust for differences between the system's sensors, filter element, oil, etc. and the reference condition. The next step is a test for remaining useful life RUL, block 72, to be described. If DPn is high enough to allow CONC to be calculated, then DPn and elapsed time data are used to calculate the regression constants and the regression equation is used to calculate RUL. Current DPn is compared to an historical empirically determined reference condition based on past or lab performance of the type of filter 12 used, and CONC is calculated according to DPn, block 70. A determination is then made as to whether RUL is greater than zero, block 72, i.e. whether there is any remaining useful life. If so, the above steps are repeated. If not, then a determination is made as to whether or not DPn is too high, block 74. If so, the display signals an indication to change the filter element, block 76, and upon such change, the cleaning cycle number is decremented back to one, block 78. If DPn is not too high, a cleaning cycle is initiated, and the display indicates same, block 80, for example by displaying that cleaning is in progress, followed by incrementing of the cleaning cycle number, block 82, followed by setting of RUL equal to the service interval, block 84, and a return to the above steps.

The preferred method involves monitoring lubrication in a lubricant circulation system circulating lubricant through a filter to a lubricated component, including sensing differential pressure DPf across the filter, providing a reference section in the circulation system and sensing differential pressure DPr across the reference section, and normalizing DPf based upon DPr. In one embodiment, lubricant temperature is measured, lubricant viscosity is measured, and lubricant flow rate is calculated from DPr and the lubricant viscosity. In another embodiment, lubricant temperature is measured, lubricant flow rate is measured, and lubricant viscosity is calculated from DPr and the lubricant flow rate.

The method is effective for determining when to change or clean lubricant filter 12. Elapsed filtering time is counted at timer 48, estimated total useful life TUL and estimated remaining useful life RUL are calculated, and it is determined that the filter is due for replacement or cleaning when RUL is a given percentage of TUL, preferably ten to twenty percent. There is further provided in combination a contaminant monitor, and contaminant level is also monitored, and it is determined that the filter is due for replacement or cleaning when RUL is a given percentage of TUL in combination with a given contaminant level. In one embodiment, turbidity is monitored. In another embodiment, particle count is monitored. In another embodiment, conductivity is monitored. In another embodiment, capacitance is monitored. In another embodiment, dielectric constant is monitored. In another embodiment, DPf versus time is monitored assuming constant influent concentration, and a correlation coefficient r is calculated for changes in contaminant loading. In a further embodiment the change in differential pressure DPf across filter 12 is monitored with respect to time. In the preferred form of this embodiment, the rate of change of DPf is monitored, for example to ascertain when the pressure drop begins to change, for example as shown at 86 in FIG. 2, particularly the rate thereof. The noted condition in the circulation system is evaluated by a series of sequential operations provided by the noted algorithm, as shown in FIG. 3, implemented in electronic controller 22 evaluating the output of the sensors. It is also contemplated that the invention may be used in conjunction with an algorithm in a neural network to process data and/or an expert system approach to diagnosis, i.e. smart systems with programmed intelligence in decision making steps. The system can be used for both engine and hydraulic systems. In hydraulics, the filter is often after the component and before the sump, rather than after the sump and before the component.

Figure 4:
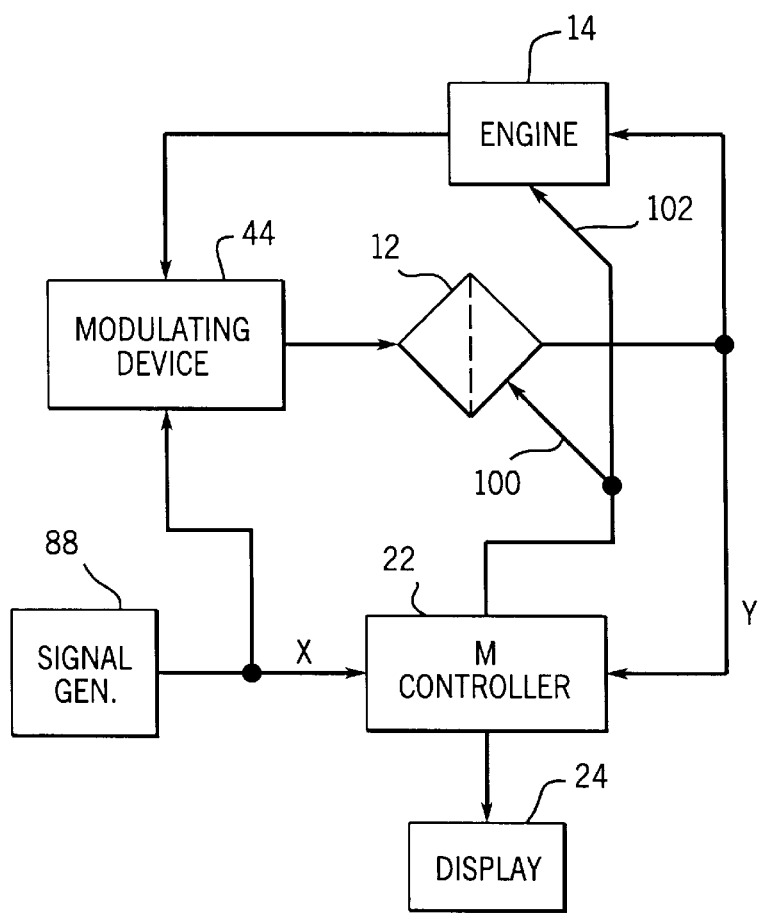
FIGS. 4 and 5 are flow charts illustrating relationships of the controller to a filter, lubricated engine component and modulating device with this invention and the prior art, respectively.
Figure 5:
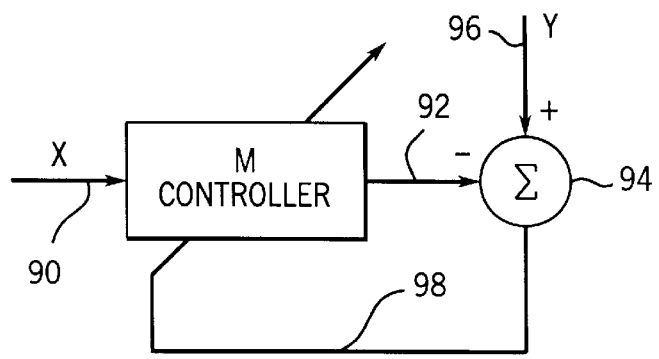

An alternative embodiment is shown in FIG. 4. The controller 22 is used to implement a model M. A modulation device 44 such as a fluctuating valve is inserted in the flow stream. The modulation device could modulate a parameter such as flow using a valve or the pump itself or could modulate some other physical parameter, such as temperature or viscosity, or chemical parameter, such as acidity, with an appropriate device or injection mechanism. The output of the sensor such as 32, 38, 34, 40, 28 following the filter is used to form a dynamic model with response characteristic $M=F/(1-FE)$ where M is the response of the model, F is the response of the filter, and E is the response of the engine. This model may be determined either in the time domain using an adaptive filter based on an algorithm such as the LMS algorithm or in the frequency domain using the Fast Fourier Transform (FFT) algorithm, for example as shown in U.S. Pat. Nos. 4,677,676, 4,987,598, 5,172,416, 5,386,477, 5,396,561, 5,557,682, 5,561,598, 5,586,189, 5,586,190, all incorporated herein by reference. FIG. 5 further shows the controller model of FIG. 4 in the form shown in the incorporated patents, to facilitate understanding of the active adaptive control techniques enabled by the present invention. In FIG. 5, model M controller 22 corresponds to model 40 of incorporated U.S. Pat. Nos. 4,677,676 and 4,987,598, model input 90 at x from signal generator 88 corresponds to model input 42 in the '676 and '598 patents, model output 92 corresponds to model output 46 in the '676 and '598 patents, and is combined at summer 94 corresponding to summer 18 in the '676 and '598 patents with the output y at 96 of the plant or function being modeled, as noted above and for example as shown at plant or acoustic path p at 4 in the '676 and '598 patents, and the output of summer 94 provides the error signal at 98 corresponding to error signal 44 in the '676 and '598 patents. Analysis of the model using look-up tables or other programmed intelligence enable diagnosis of the condition of the lubricant, filter, and component.

The results of the analysis of the model may be displayed in a suitable manner using a liquid crystal display (LCD), light emitting diodes (LED) or similar device to enable appropriate action to be taken by the system operator or maintenance personnel. Alternatively, the controller can be used to generate an output at 100 that automatically services the filter system through initiation of a cleaning cycle or other appropriate action, for example as in above noted U.S. Pat. No. 5,462,679 and U.S. applications Ser. No. 08/755,479, filed Nov. 22, 1996, Ser. No. 08/755,497, filed Nov. 22, 1996 now U.S. Pat. No. 5,779,900, and Ser. No. 08/819,296, filed Mar. 18, 1997 , now U.S. Pat. No. 5,858,224. Alternatively, the controller output can be connected to the engine at 102 or other lubricated component to directly control its function in response to the analysis of the controller system or to communicate with the overall engine diagnostic maintenance system.

It is recognized that various equivalents, alternatives and modifications are possible within the scope of the appended claims.

We claim:

1. A lubrication system comprising a circulation system circulating lubricant to a lubricated work-generating component, a filter in said circulation system filtering said lubricant, a combination of sensors operable for sensing a condition of said lubricant before and after passage through said filter and sensing said condition before and after passage through said component and providing an output indicative of a condition in said circulation system.

2. The lubrication system according to claim 1 wherein said condition in said circulation system is a condition of said component.

3. The lubrication system according to claim 1 wherein said circulation system comprises a sump providing a collection reservoir for said lubricant, a pump pumping lubricant from said sump through said system, and a return line returning lubricant to said sump, and wherein said combination of sensors comprises first, second and third sensors, one of which is between said filter and said component.

4. The lubrication system according to claim 3 wherein said pump pumps lubricant from said sump through said filter to said component, said return line returns lubricant from said component to said sump, said first sensor is between said pump and said filter, said second sensor is between said filter and said component, and said third sensor is between said component and said sump.

5. The lubrication system according to claim 3 wherein said combination of sensors comprises a fourth sensor comprising a pressure differential sensor sensing differential pressure across said filter.

6. The lubrication system according to claim 3 wherein each of said first, second and third sensors is a contamination monitor.

7. The lubrication system according to claim 3 wherein each of said first, second and third sensors is a turbidimeter.

8. The lubrication system according to claim 3 wherein each of said first, second and third sensors is a capacitance sensor.

9. The lubrication system according to claim 3 wherein each of said first, second and third sensors is a dielectric constant sensor.

10. The lubrication system according to claim 3 wherein each of said first, second and third sensors is an optical monitor.

11. The lubrication system according to claim 1 wherein said condition in said circulation system is evaluated by a series of sequential operations provided by an algorithm.

12. A method of actively monitoring a lubricated work-generating component in a circulation system circulating lubricant through a filter to said component, comprising comparing influent to said component with effluent from said component to ascertain how lubricant is modified by said component, by sensing a condition of said lubricant passing through said filter, providing a plurality of sensors and sensing a condition of said lubricant before and after passing through said filter and before and after passage through said component.

13. The method according to claim 12 wherein said circulation system includes a first path passing lubricant from said filter to said component, and a second path passing lubricant from said component back to said filter, and comprising providing a first set of one or more sensors in said first path and sensing a condition of said lubricant after passage through said filter and before passage through said component, and providing a second set of one or more sensors in said second path and sensing a condition of said lubricant after passage through said component and before passage through said filter.

14. A method of actively monitoring a lubricated component in a circulation system circulating lubricant through a filter to said component, comprising comparing influent to said component with effluent from said component to ascertain how lubricant is modified by said component, by sensing a condition of lubricant passing through said filter wherein said circulation system includes a first path passing lubricant from said filter to said component, and a second path passing lubricant from said component back to said filter, and comprising providing a first set of one or more sensors in said first path and sensing a condition of said lubricant after passage through said filter and before passage through said component, and providing a second set of one or more sensors in said second path and sensing a condition of said lubricant after passage through said component and before passage through said filter, modulating the flow of lubricant to said component to facilitate said sensing and testing of said active monitoring.

15. A method of using a lubricant filter as a sensor in a circulation system circulating lubricant through said filter to a lubricated work-generating component, comprising sensing a condition of lubricant passing through said filter with a first sensor, providing a reference section in said circulation system and sensing a condition of lubricant passing through said reference section with a second sensor, comparing the outputs of said first and second sensors and determining a given condition in said circulation system, and comprising:

a) sensing differential pressure DPr across said reference section;

b) sensing differential pressure DPf across said filter;

b) sensing differential pressure DPf across said filter;

c) counting elapsed time T;

d) determining a normalized differential pressure DPn according to the ratio of DPf to DPr e) determining if DPn is stable,
  1) and if not, returning to steps a) through d)
  2) and if so, then continuing with the following step;

f) determining if DPn is above a given value high enough to allow contaminant concentration CONC to be calculated,
  1) and if not, then monitoring DPn as a function of time and calculating remaining useful life RUL according to service interval minus T,
  2) and if so, then
    a) calculating regression constants for a regression equation for DPn as a function of time,
    b) calculating CONC and RUL using the regression equation and DPn.

16. The method according to claim 15 comprising:
determining if RUL is greater than zero,
and if so, then returning to steps a) thorough f) and if not, then determining if DPn is a service-change value,
and if so, then determining that the filter should be replaced,
and if not, then determining that the filter should be cleaned.

17. The method according to claim 15 comprising, in step f), calibrating a regression model by comparing DPn and a reference condition.

18. A method for monitoring contamination in a lubricant circulation system circulating lubricant through a filter to a lubricated component, comprising providing a combination of contaminant sensors sensing contamination of said lubricant before and after passage through said filter and before and after passage through said component, and evaluating the output of said sensors including comprising determination of gross contamination level of said lubricant, solids contamination, amplitude and frequency of excursions from said baseline, and noise due to operation of said component.

19. The method according to claim 18 comprising evaluating the output of said sensors by a series of sequential operations provided by an algorithm.

20. A lubrication system comprising a circulation system circulating lubricant to a lubricated work-generating component, a modulating device modulating lubricant circulation to provide a modulated condition, a sensor detecting said modulated condition a filter for removing contaminants from said lubricant, and means for forming a dynamic model from output from said sensor enabling diagnosis of the condition of the lubricant, filter and component.

21. The lubrication system according to claim 20 wherein said modulating device is responsive to said sensor.

22. The lubrication system according to claim 20 wherein the output of said sensor is evaluated with an algorithm.

23. The lubrication system according to claim 22 wherein the results of said evaluation are displayed to provide maintenance information.

24. The lubrication system according to claim 22 wherein the results of said evaluation are used to control a cleaning cycle of said filter.

25. The lubrication system according to claim 22 wherein said component comprises an engine, and wherein the results of said evaluation are used to enhance operation of an engine diagnostic maintenance system.

26. The lubrication system according to claim 20 wherein said algorithm comprises an adaptive filter model.

27. The lubrication system according to claim 26 wherein said adaptive filter model models said circulation system.

28. A lubrication system comprising a circulation system circulating lubricant to a lubricated component, a modulating device modulating lubricant circulation to provide a modulated condition, a sensor detecting said modulating condition a filter for removing contaminants from said lubricant, and means for evaluating the output of said sensor utilizing an algorithm which performs frequency response analysis enabling diagnosis of the condition of the lubricant, filter and component.

29. The lubrication system according to claim 28 wherein said frequency response analysis uses a Fast Fourier Transform.

* * * * *